United States Patent
Khouri

(10) Patent No.: US 9,095,297 B2
(45) Date of Patent: Aug. 4, 2015

(54) ILLUMINATED DENTAL PROP

(71) Applicant: Louie Khouri, Birmingham, MI (US)

(72) Inventor: Louie Khouri, Birmingham, MI (US)

( * ) Notice: Subject to any disclaimer, the term of this patent is extended or adjusted under 35 U.S.C. 154(b) by 260 days.

(21) Appl. No.: 13/771,597

(22) Filed: Feb. 20, 2013

(65) Prior Publication Data
US 2013/0164702 A1    Jun. 27, 2013

Related U.S. Application Data

(63) Continuation-in-part of application No. 11/877,982, filed on Oct. 24, 2007, now Pat. No. 8,905,924.

(60) Provisional application No. 60/862,660, filed on Oct. 24, 2006.

(51) Int. Cl.
*A61B 1/24*   (2006.01)
*A61B 1/06*   (2006.01)
*A61C 5/14*   (2006.01)

(52) U.S. Cl.
CPC ............. *A61B 1/24* (2013.01); *A61B 1/0684* (2013.01); *A61C 5/14* (2013.01)

(58) Field of Classification Search
CPC .......................................................... A61B 1/24
USPC ....................................... 600/238; 433/29, 31
See application file for complete search history.

(56) References Cited

U.S. PATENT DOCUMENTS 2,528,458 A * 10/1950 Stone ............................ 600/212

* cited by examiner

*Primary Examiner* — Christian Sevilla
(74) *Attorney, Agent, or Firm* — Harness, Dickey & Pierce, PLC

(57) ABSTRACT

The present invention relates to an illuminated dental prop for holding a patient's mouth open during dental procedures. The illuminated dental prop is completely disposed within the patient's mouth during use and includes a body portion and a lighting assembly that is selectively detachable from the body to allow for intense sterilization of the components after use. Under certain embodiments of the invention, the body portion and/or the lighting assembly will be disposable after a single use.

16 Claims, 5 Drawing Sheets

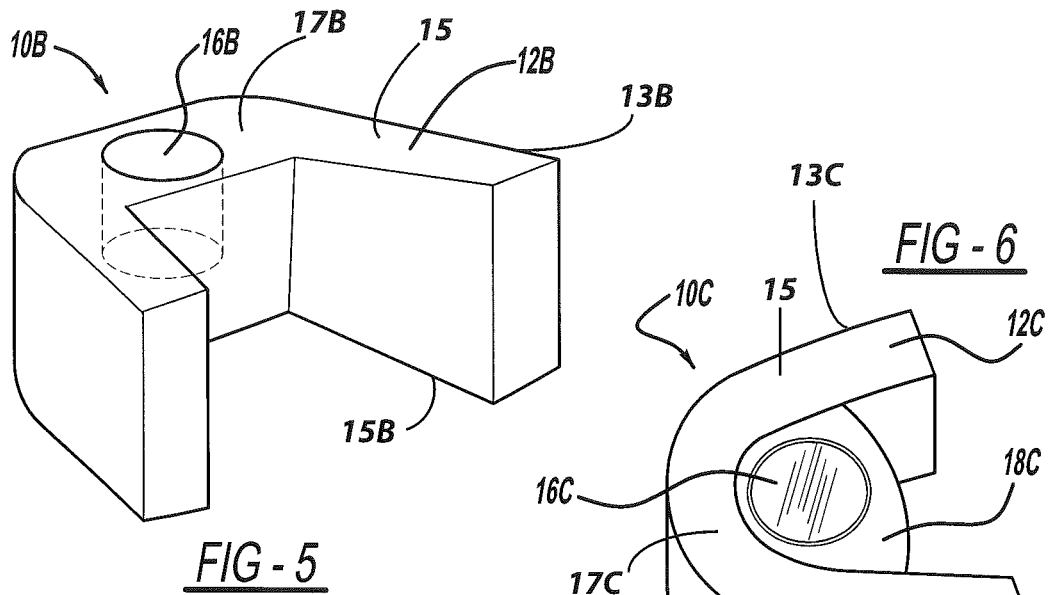
FIG-5
FIG-6
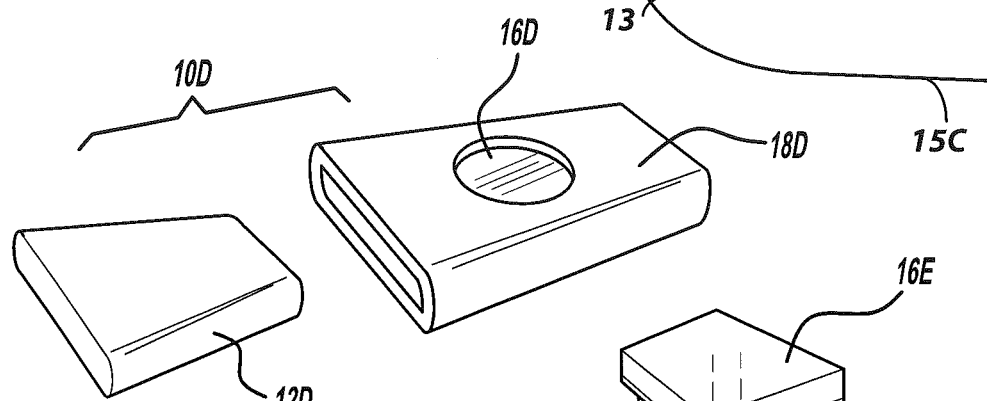
FIG-7
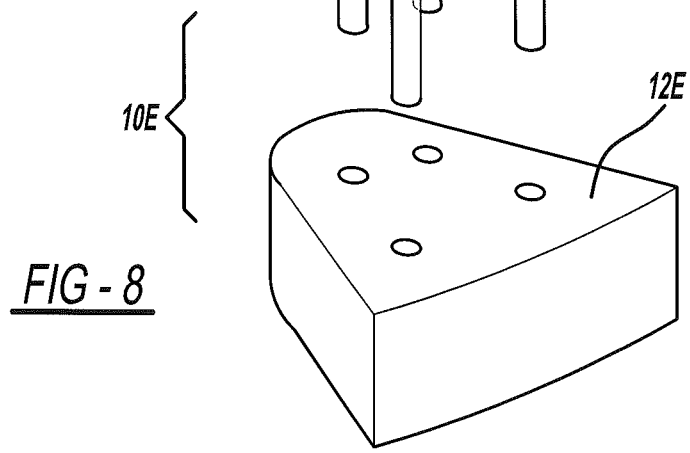
FIG-8

ILLUMINATED DENTAL PROP

BACKGROUND

1. Field of the Invention

The present invention generally relates to illuminated dental props for holding the mouth open during dental procedures. Dental props, per se, are known to come in a variety of shapes and sizes such as wedge-shaped props and C-shaped props by way of non-limiting example. Generally the props are placed between the upper and lower teeth, opposite the side of the mouth which needs to be accessed by a dental practitioner. However, with regard to accessing and viewing the target area by the dental practitioner, currently available dental props do nothing to enhance the visibility within the oral cavity to carryout the necessary procedure.

Further, while various light sources are available to assist in illuminating the oral cavity, such devices are positioned outside of the oral cavity with the light source directed at the target area. However, external light sources tend to be somewhat ineffective. Thus, the present invention relates to the incorporation of a light assembly with a dental prop of desired size and shape.

2. Description of the Prior Art

Relatively recently a handful of patents and patent applications directed to the general concept of combining a light source with a dental prop have surfaced. One such patent is U.S. Pat. No. 6,332,776 which issued Dec. 6, 2001 to Martin et al. According to one embodiment disclosed, a unitary body formed to include a first cavity having an inclined reflective surface is disclosed. Light projecting from a light source connected to a light conducting cable is projected upon the reflective surface to emit light within the patient's mouth. Under a second embodiment, a dental prop is constructed including a cavity which hosts the lighting elements including a primary induction coil connected to a secondary induction coil. Under all embodiments disclosed, there does not appear to be any teaching or disclosure of a light assembly which is conveniently detachable from the body of the dental prop.

Alternatively, US Patent Publication No. US/2005/0239018 discloses a lighted dental prop wherein the light source is integrated in a permanently fixed relationship with the body of the bite block. Under this scenario, either the entire construction would be discarded after a single use or the product as a whole is sterilized for reuse. There does not appear to be any disclosure as to replacement of the light source if need be which is another apparent design flaw.

A perceived problem with each of the above-referenced teachings is that the light source is not readily removable from the bite block such that the bite block portion can be sterilized or discarded after a single use. Further, the light assembly is either integral with the bite block portion or requires extreme work to detach the same from the bite block.

SUMMARY

The present invention provides for an illuminated dental prop for holding the dental patient's mouth open during dental procedures which incorporates a selectively removable light source. In addition to providing much needed light to the oral cavity of a patient, a significant advantage over the above noted references is the ability to readily remove the light assembly from the bite block to facilitate sterilization of the light assembly and, under certain embodiments, discarding of the bite block portion. The dental props of the present invention are designed to be of a size and geometry to be fully contained within the patient's mouth, i.e., without wires extending out of the mouth, to ensure clearance in the oral cavity of the patient such that the practitioner can access the target area with the necessary dental instruments.

DRAWINGS

The drawings described herein are for illustration purposes only and are not intended to limit the scope of the present disclosure in any way.

FIG. 5 is a perspective view of an alternate illuminated dental prop;

FIG. 6 is a perspective view of an alternative illuminated dental prop wherein the light assembly is retro-fit to an existing convention dental prop;

FIG. 7 is an alternative illuminated dental prop assembly including a lighted sleeve disposable over the body of a dental prop;

FIG. 8 is an alternative illuminated dental prop assembly including a lighted pliable attachment disposable over the body of a dental prop;

DETAILED DESCRIPTION

Figure 1:
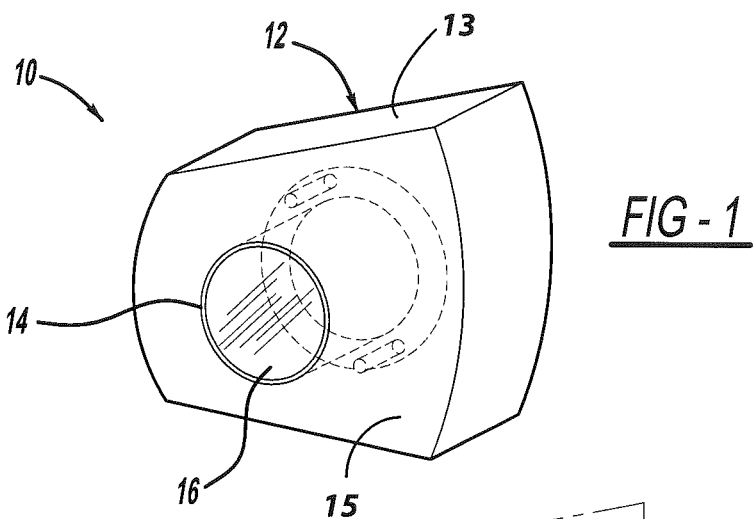
FIG. 1 is a perspective view of a first embodiment of the illuminated dental prop assembly.

The following description is merely exemplary in nature and is not intended to limit the present disclosure, application, or uses. It should be understood that throughout the drawings, corresponding reference numerals indicate like or corresponding parts and features.

Figure 2:
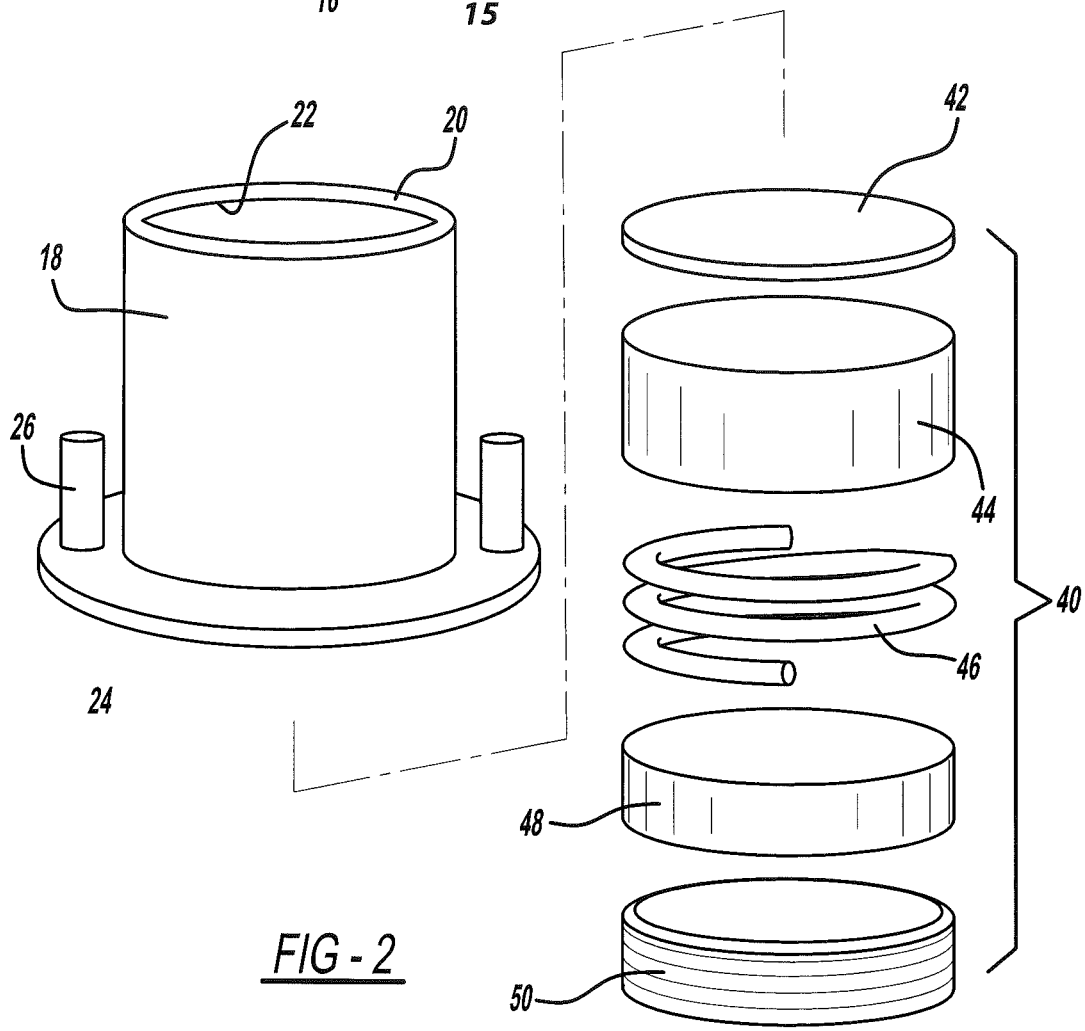
FIG. 2 is a blown apart perspective view of the illuminated dental prop of FIG. 1.
Figure 3:
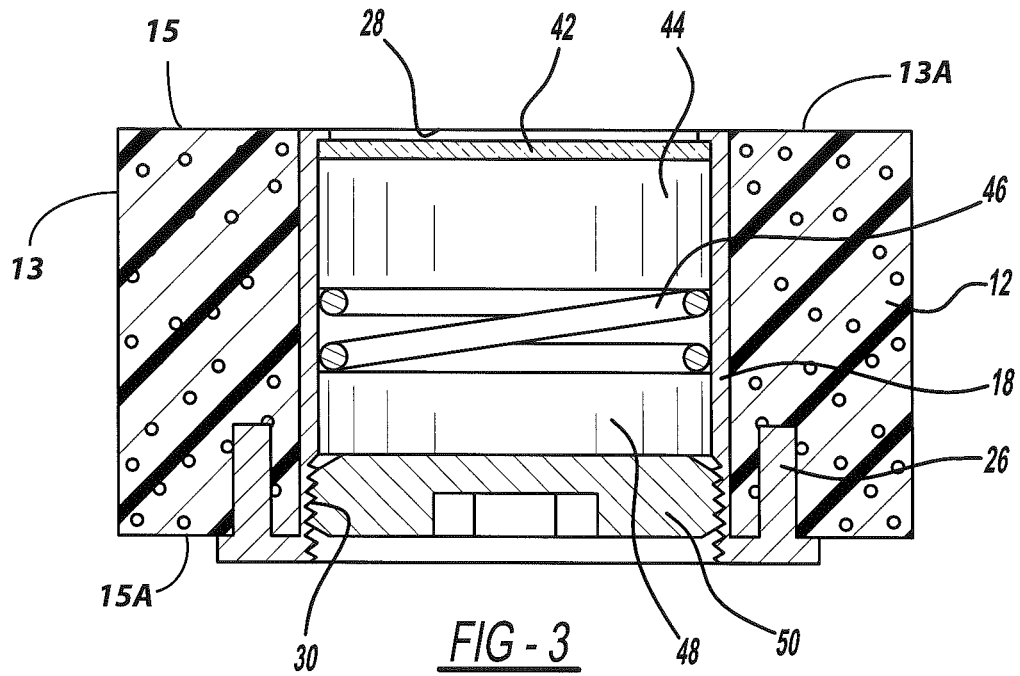
FIG. 3 is a sectional view of the illuminated dental prop assembly of FIGS. 1 and 2.

The first illuminated dental prop in accordance with the teachings of the present invention is shown with reference to FIGS. 1-3. Initially, referring to FIG. 1, there is shown the illuminated dental prop 10 which includes a body 12 which forms the bite block portion of the assembly and a light assembly 16 which is mounted through an aperture 14 of the body 12. The body 12 can be in many shapes or configurations and is shown according to the first embodiment as a wedge-shaped bite block having upper and lower teeth engaging surfaces 13 and 13A and first and second substantially perpendicular sidewalls 15 and 15A. The light assembly 16 which is selectively detachable from the body of the bite block generally includes a housing 18 and a light source 40. The housing 18 includes a sleeve 20 including a longitudinally central bore 22 for hosting the light source 40. The sleeve 20 includes in inwardly extending lip 28 at one end and a threaded interior lead-in portion 30 along the opposite end of lip 28. The housing 18 also includes an integral outwardly extending flange disposed along the end opposite lip 28 which may optionally include one or more posts 26 which seat into the body 12 of the bite block to assist in securing the lighting assembly.

The light source 40 according to the first embodiment 10 generally includes a lens 42 disposed against the inwardly extending lip 28 of the housing 18, a lighting element 44, an electrical contact 46, a battery 48, and a threaded end cap 50. As should be understood by those skilled in the art, as the threaded end cap 50 is rotated to an extent such that the battery is in sufficient electrical contact with the lighting element through electrical contact 46, the lighting element 44 becomes illuminated and remains illuminated until such time that the threaded end cap is sufficiently backed away. According to this embodiment, the lighting element 44 is in the form of a miniature light bulb; however, as will be described in further detail below, alternative lighting means may be utilized.

Figure 4:
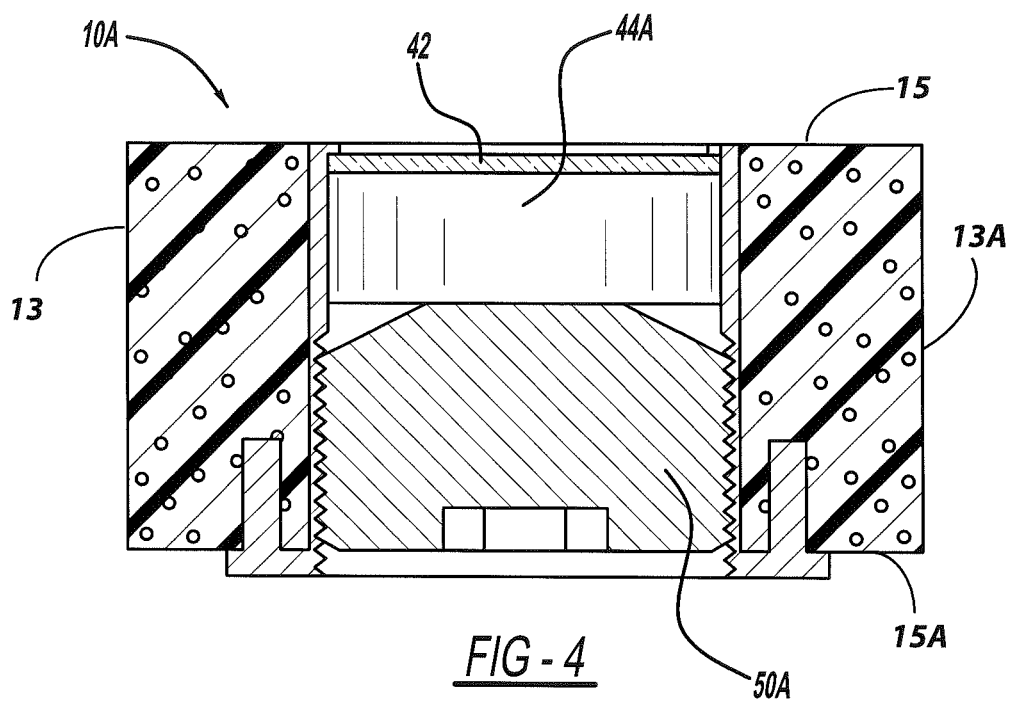
FIG. 4 is a sectional view of an alternative illuminated dental prop featuring a different lighting assembly.

Referring to FIG. 4, there is shown a first alternative illuminated dental prop embodiment 10A wherein the lighting element 44A is activated by the threaded end cap 50A which is in the form of an induction element. As should be understood by those skilled in the art, the induction element 50A is activated by another induction coil (not shown) via electromagnetic energy.

In addition to the dental props shown in FIGS. 1-3 and 4, respectively, it should be understood that the lighting assembly may be employed with those or other dental prop bodies. For example, the lighting assembly may be an LED light package including an LED light source and a battery. This assembly may be two separate components or may be in the form of a self-contained assembly which is attached to the dental prop body. Whatever light assembly is employed, it is envisioned the light assembly will have a useful life which affords the end user the option of reusing the light assembly after appropriate sterilization by inserting it into a fresh dental prop body. Thus, a kit having at least one selectably reusable light assembly along with a plurality of disposable dental props may be provided commercially.

Alternately, a reusable dental prop with a plurality of detachable, disposable light assemblies is also envisioned.

Regardless of the dental prop body design, generally the upper and lower teeth will sit in a stable position on the respective upper and lower teeth engaging surface.

Referring to FIG. 5, there is yet another alternative embodiment 10B which includes a lighting assembly 16B disposed within an operative along a central portion of the body 12B of the bite block assembly. As can be seen from FIG. 5, the body is substantially C-shaped such that the bite block provides sufficient clearance so that it does not interfere with the dental practitioner during a dental procedure. Thus, the C-shaped body is defined by first and second forward projecting portions which are engaged by the teeth 13 and 13B (teeth engaging services), a central body portion 17B which is positioned toward the back of the mouth and sidewalls 15 and 15B.

Referring to FIG. 6, yet another alternative embodiment 10C is depicted. The body 12C also generally has a C-shaped body and the lighting assembly 16C, rather than being embedded within the body, is in the form of a selectively detachable unit which is mounted within the concave recess along the interior wall of the body 12C. The body includes teeth engaging surfaces 13 and 13C, a central body portion 17C and first and second sidewalls 15 and 15C on opposite sides of the body. This embodiment is considered to be an option for retro-fitting currently commercially available bite blocks. The lighting assembly 16C may be mechanically attached via a male and female coupling with the body or adhesively attached within the recess.

Referring to the embodiment of FIG. 7 referenced by the numeral 10D, the bite block body 12D fits within a pliable sheath. The sheath serves as the housing 18D and hosts the lighting assembly 16D.

Referring to FIG. 8, another embodiment 10E is depicted wherein the body 12E includes a plurality of openings for receiving the platform-type housing 18E having mounted thereto a light assembly 16E.

Figure 9:
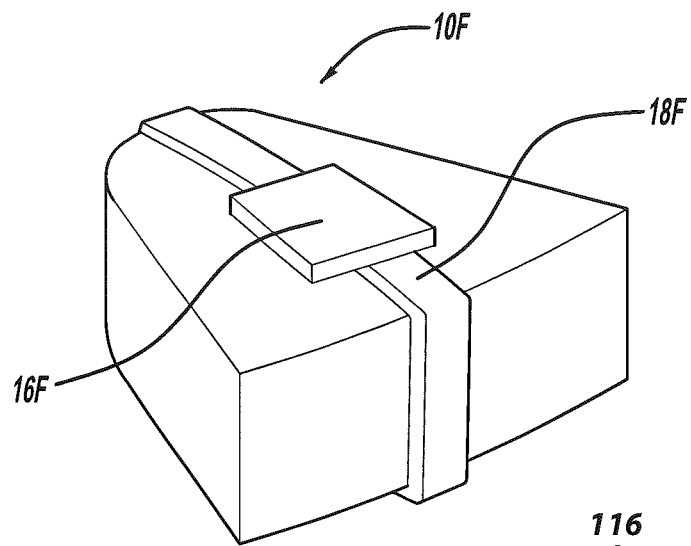
FIG. 9 is an alternative illuminated dental prop assembly including a lighted band disposable over the body of a dental prop.

Referring to FIG. 9, another embodiment 10F is shown as including a housing 18F in the form of a band having attached thereto a light assembly 16F. The band can be formed from various materials including elastic by way of non-limiting example. This type of structure would be ideal for retro-fitting commercially available bite blocks including wedges as well as C-shaped bite blocks with lighting to illuminate the oral cavity.

The illuminated dental props of FIGS. 6-9, preferably employ a self contained LED light as the light source. As should be understood by those skilled in the art, the LED lighting should illuminate the oral cavity to an appreciably extent but, should not generate light that falls within the light range that would promote undesired curing of any materials employed in the dental procedure being carried out. Additionally, the lighting assembly shall not generate as unacceptable level of heat which could be uncomfortable to a patient.

The body 12C which is generally formed from a moldable thermoplastic, thermoset or elastomeric material may include a slot (not shown) along the concave recess into which the lighting assembly 16C is press fit. The slot may include a locking mechanism such that when the lighting assembly is disposed therein the battery will be activated.

Figure 10:
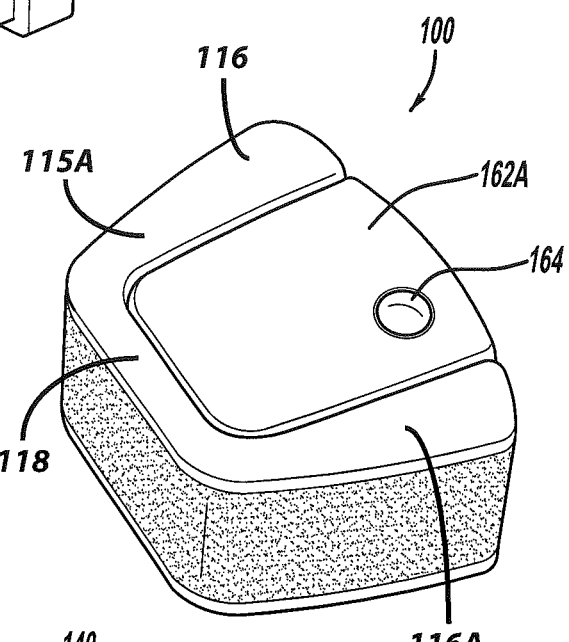
FIG. 10 is an alternative illuminated dental prop assembly including a dental prop and a selectively removable light assembly.
Figure 11:
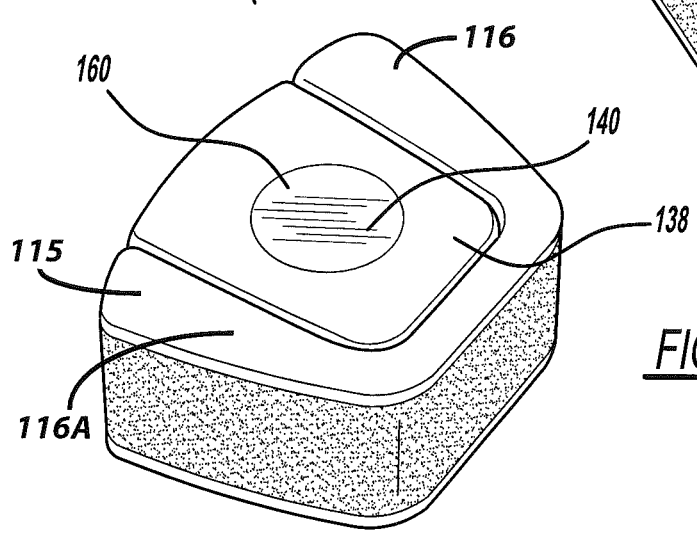
FIG. 11 is a perspective view of the embodiment of FIG. 10.
Figure 12:
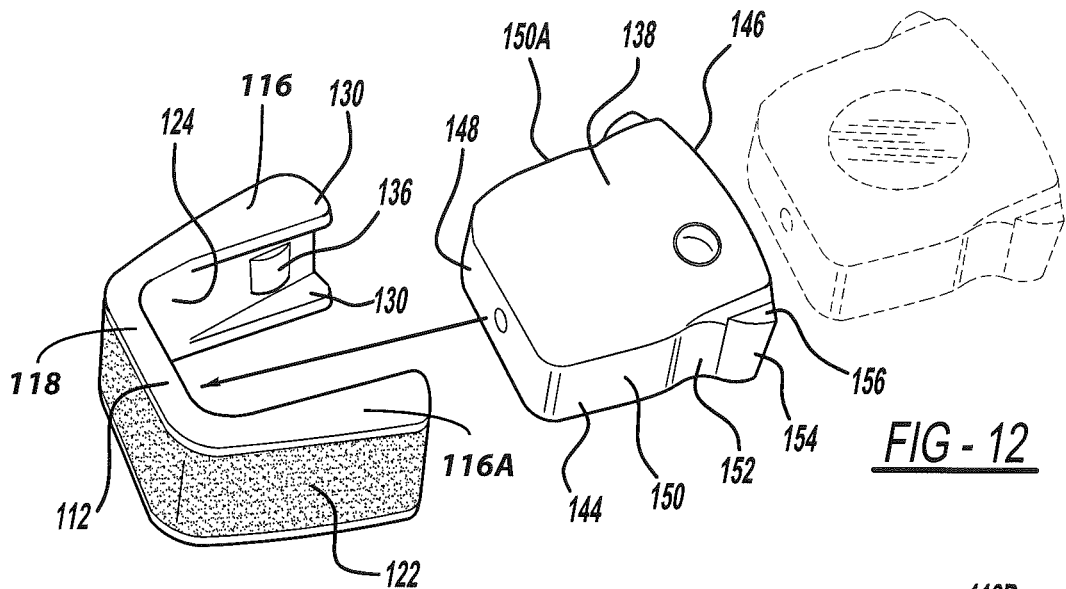
FIG. 12 is a perspective view showing the dental prop and light assembly separated.

Referring to FIGS. 10-12, there is shown an alternative illuminated dental prop embodiment 100 including two major components, a bite prop 112 and a light assembly 114. The light assembly, as with other embodiments shown herein, includes as its main components a housing 138 and a lighting source 140. The housing can be formed from a variety of materials sufficient to protect the lighting package secured within, such as lightweight thermoplastics, thermosets or silicone, by way of non-limiting example. The light source is preferably a LED light.

As shown, the lighting assembly housing 138 has an exterior wall 144 defined by a front wall 146, rear wall 148 and opposing top and bottom walls 150, 150A, respectively. The top and bottom walls in the embodiment shown are mirror images, both including a recess 152 which receives the tabs 126 projecting from the interior wall of the bite prop. The top and bottom walls also include a flange 154 located proximate to the front wall 146 which has offset sides 156. As also shown, the light assembly includes a translucent area 160 through which the light generated by the light assembly is transmitted. The area can be limited to help focus the light or can take up a larger portion of the sidewall 162. The light assembly will also typically include an on/off button or switch 164 shown here on the opposing sidewall 162A.

The bite prop 112 has a substantially C-shaped body including first and second legs, 116 and 116A, respectively, extending at an inclined angle from the traverse portion 118 to define an open area 132 which ultimately is occupied by the light assembly. The body also includes first and second sidewalls 115 and 115A. This slight angle allows the light assembly to be more easily inserted into the opening or open area for engagement with the bite prop. The external wall 120 extending along the transverse portion 118 and first and second legs 116, 116A of the prop 100, optionally, but preferably, include an enhanced tooth engaging surface 122. Thus, when the dental prop 100 is positioned over the patient's teeth at the back of the mouth, with the transverse portion near the back and the first and second legs projecting toward the front of the mouth, the extra grip provided along the external wall 120, in association with the patient's natural instinct to close their jaw, helps keep the prop fixed over the teeth. The tooth engaging surface 122 can be formed as an integral part of the body in the form of a roughened surface or may be an over-molded piece of elastomeric material having a roughened surface.

The interior wall 124 of the bite prop which extends along the transverse portion 118 and the first and second legs 116, 116A is sized to tightly accommodate the light assembly 114 when it is fully inserted therein. As such, the interior wall 124 is in close contact with the exterior wall 144 of the light assembly 114 during use. An enhanced locking feature is also offered by one or more tabs 126 extending from the interior wall which mate with a complementary recess 152 provided along the exterior wall of the light assembly. As shown, it is preferable that there be at least one tab along the first and second legs and at least one recess along the top and bottom walls of the exterior wall. While not shown, it should be understood that the interior wall may have at least one recess and the exterior wall of the light assembly may host one or more locking tabs.

Yet another feature of the bite prop are the truncated sidewalls 130 that extend from at least one and preferably both of the legs 116 and 116A into the opening 132 which is ultimately filled by the light assembly during use. The truncated sidewalls 130 seat against the offset sides 156 of the flange 154 of the light assembly body when the light assembly is fully inserted into the opening 132. As should be appreciated, while the overall design of the illuminated dental prop makes it easy to mate and remove the light assembly from the dental prop, it is highly secure when the light assembly is fully engaged within the opening of the dental prop.

Figure 13:
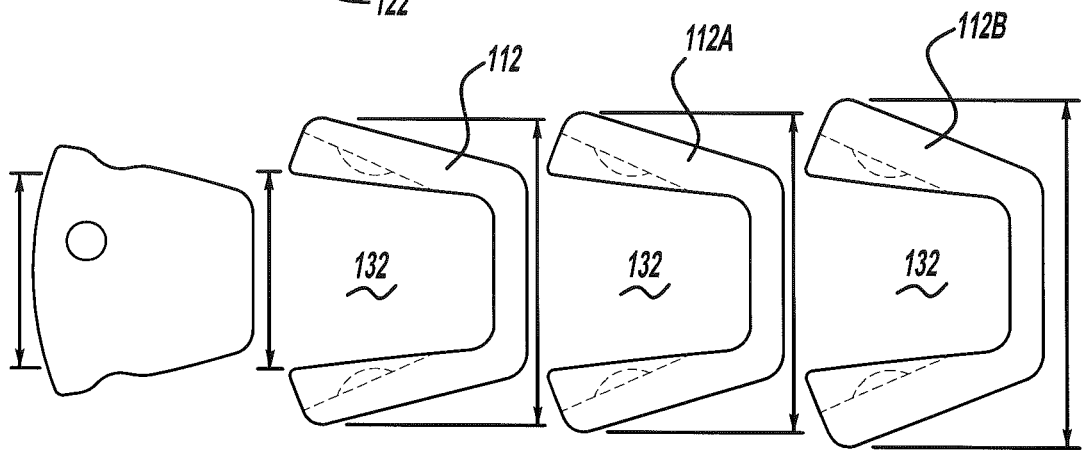
FIG. 13 shows dental props of different sizes which are capable of hosting a standard light assembly.

Referring to FIG. 13, there are shown a plurality of bite props 112, 112A and 112B each of which are progressively larger and serve to accommodate patient's having small, medium and large sized oral cavities. By design, the inner dimension, e.g., the inner wall of the bite prop, remains the same size so that a single light assembly can be used with dental props sized to different patients. Thus, the illuminated dental prop can be offered as a kit.

Figure 14:
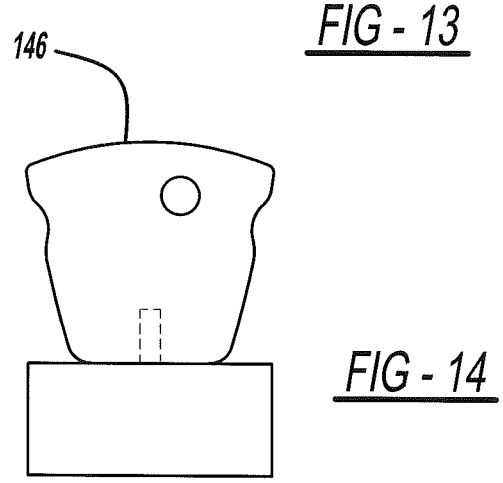
FIG. 14 shows an embodiment when the light assembly is rechargeable.

Referring to FIG. 14, it is demonstrated that under one embodiment, the light assembly includes a receptacle for receiving a battery charger, however, it is also contemplated that the light assembly can be of the type which is capable of being recharged using an induction type system. Still further, as discussed above, the light assembly may include replaceable batteries or may be replaced with another light assembly when the charge of the batteries is exhausted.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An illuminated dental prop for lighting a patient's mouth comprising:
    a lighting assembly including a housing and a light emitting diode (LED) light source; and
    a bite prop which houses said lighting assembly during use, said bite prop having a body including at least one teeth engaging surface and an inner wall defining an opening for receiving the lighting assembly, said dental prop being seized to maintain a patient's mouth in an open position during use.

2. The illuminated dental prop of claim 1 wherein the body of the light assembly is formed from a material selected from the group consisting of thermoplastic, thermosets and silicone.

3. The illuminated dental prop of claim 1 wherein the body of the light assembly includes a translucent portion through which light generated by the light source is transmitted.

4. The illuminated dental prop of claim 1 wherein the bite prop includes first and second legs extending from a transverse portion which defines a substantially C-shaped opening for receiving the light assembly.

5. The illuminated dental prop of claim 4 wherein at least one of said first and second legs include a truncated wall extending into the opening to hold the light assembly.

6. The illuminated dental prop of claim 4 wherein said bite prop includes an inner wall occurring along the first and second legs and said transverse, said inner wall including at least one inwardly projecting tab which engages the light assembly housing to further secure the light assembly in contact with said bite prop.

7. The illuminated dental prop for lighting a patient's mouth comprising:
    a substantially C-shaped bite prop defined by first and second legs extending from a transverse portion having an inner wall thereby defining an open area between said legs, at least one of said legs include one or more sidewalls extending into the open area; and
    a light assembly including a housing having a translucent portion and a light source, said housing being shaped to tightly fit within the open area adjacent the inner wall of the bite prop and being secured therewith by said one or more sidewalls.

8. The illuminated dental prop of claim 7 wherein the one or more sidewalls include a pair of spaced sidewalls occurring along at least one of the first and second legs.

9. The illuminated dental prop of claim 8 wherein both the first and second legs include at least one sidewall.

10. The illuminated dental prop of claim 7 wherein said inner wall includes a tab extending toward the open area and the light assembly housing includes a recess which mates with the tab of the bite prop upon sufficient insertion of the light assembly into the open area of the bite prop.

11. The illuminated dental prop of claim 10 wherein the tab occurs along the inner wall along one of said first and second legs.

12. The illuminated dental prop of claim 11 wherein said bite prop includes a tab on both said first and second legs which mates with corresponding recesses on the light assembly.

13. The illuminated dental prop of claim 1 wherein said LED light source is rechargeable.

14. The illuminated dental prop of claim 7 wherein said light source is rechargeable.

15. The illuminated dental prop of claim 7 wherein said light source is a light emitting diode (LED).

16. The illuminated dental prop of claim 7 wherein the bite prop is formed from a material selected from the group consisting of thermoplastic, thermosets and silicone.

* * * * *